(12) United States Patent
Sugimoto et al.

(10) Patent No.: US 8,821,934 B2
(45) Date of Patent: Sep. 2, 2014

(54) PULLULAN-CONTAINING POWDER, PROCESS FOR PRODUCING THE SAME AND USE THEREOF

(75) Inventors: Toshiyuki Sugimoto, Okayama (JP); Toshio Miyake, Okayama (JP)

(73) Assignee: Hayashibara Co., Ltd., Okayama-Shi, Okayama (JP)

( * ) Notice: Subject to any disclaimer, the term of this patent is extended or adjusted under 35 U.S.C. 154(b) by 2111 days.

(21) Appl. No.: 10/484,216

(22) PCT Filed: Jul. 17, 2002

(86) PCT No.: PCT/JP02/07271
§ 371 (c)(1),
(2), (4) Date: Jan. 20, 2004

(87) PCT Pub. No.: WO03/008495
PCT Pub. Date: Jan. 30, 2003

(65) Prior Publication Data
US 2004/0197410 A1    Oct. 7, 2004

(30) Foreign Application Priority Data

Jul. 19, 2001  (JP) .................................. 2001-220683
Oct. 5, 2001   (JP) .................................. 2001-309759

(51) Int. Cl.
*A61K 9/14*    (2006.01)
*C12P 19/10*   (2006.01)
*C07H 1/00*    (2006.01)

(52) U.S. Cl.
USPC ...................... 424/489; 435/102; 536/123.12

(58) Field of Classification Search
USPC ..................... 424/489; 435/102; 536/123.12
See application file for complete search history.

(56) References Cited

U.S. PATENT DOCUMENTS

| | | | | |
|---|---|---|---|---|
| 5,411,945 | A * | 5/1995 | Ozaki et al. ...................... | 514/23 |
| 5,919,668 | A * | 7/1999 | Mandai et al. .................. | 435/97 |
| 5,922,580 | A * | 7/1999 | Maruta et al. .................. | 435/100 |
| 6,005,100 | A * | 12/1999 | Mandai et al. ............ | 536/123.13 |
| 7,192,746 | B2 * | 3/2007 | Kubota et al. ................... | 435/97 |

FOREIGN PATENT DOCUMENTS

| | | |
|---|---|---|
| EP | 0 090 356 A1 | 10/1983 |
| EP | 0 559 450 A2 | 9/1993 |
| EP | 0 628 630 A2 | 12/1994 |
| EP | 0 636 693 A2 | 2/1995 |
| EP | 0 868 916 A2 | 10/1998 |
| EP | 1 159 882 A2 | 12/2001 |
| EP | 1 229 112 A1 | 8/2002 |
| EP | 1 398 346 A1 | 3/2004 |
| JP | 216695/83 | 12/1983 |
| JP | 236860/87 A | 10/1987 |
| JP | 164858/88 A | 7/1988 |
| JP | 197432/89 A | 8/1989 |
| JP | 03-14519 A | 1/1991 |
| JP | 170977/95 A | 7/1995 |
| JP | 213283/95 A | 8/1995 |
| JP | 248097/95 A | 9/1995 |
| JP | 2560381 * 12/1996 | ............... A61K 9/28 |
| JP | 10-56969 A | 3/1998 |
| JP | 48765/01 A | 2/2001 |
| JP | 53807/08 A | 2/2002 |
| WO | WO 02/10361 A1 | 2/2002 |
| WO | WO 02/088246 A1 | 11/2002 |

OTHER PUBLICATIONS

Bradbrook, Gail M., et al, "X-ray structure determination and modeling of the cyclic tetrasaccharide cydo-(→6)-α-D-Glc*p*-(1→3)-α-D-Glc*p*-(1→6)-α-D-Glc*p*-(1→3)-α-D-Glc*p*-(1→)" Carbohydrate Research, vol. 329, (2000), pp. 655-665.

* cited by examiner

*Primary Examiner* — Michael G Hartley
*Assistant Examiner* — Leah Schlientz
(74) *Attorney, Agent, or Firm* — Browdy and Neimark, PLLC (57) ABSTRACT

The object of the present invention is to overcome conventional demerits of pullulan powders prepared by conventional techniques, i.e., they could not be homogeneously mixed with non-reducing saccharides composed of glucose units when mixed together, and the resulting mixtures do not easily dissolve in water; and to provide a pullulan-containing powder with an improved rate of water dissolution, as well as to provide preparations and uses thereof. The present invention solves the above object by providing a pullulan-containing powder which uniformly comprises pullulan as a main ingredient and a non-reducing saccharide, and their process and uses; wherein the pullulan-containing powder is prepared by the steps of preparing a solution dissolving pullulan and a non-reducing saccharide homogeneously, pulverizing the solution, and collecting the resulting pullulan-containing powder. The powder has an improved rate of water dissolution, while retaining satisfactory resistance to humidity without fear of causing separation between the pullulan and the non-reducing saccharide.

3 Claims, 1 Drawing Sheet

PULLULAN-CONTAINING POWDER, PROCESS FOR PRODUCING THE SAME AND USE THEREOF

TECHNICAL FIELD

The present invention relates to a pullulan-containing powder which uniformly contains pullulan and a non-reducing saccharide(s) composed of glucose units, has an improved rate of water dissolution, and retains a satisfactory resistance to humidity; and to a process for the same and use thereof.

BACKGROUND ART

As pullulan products, "PULLULAN PF-10™" with an average molecular weight of 100,000 and "PULLULAN PF-20™" with an average molecular weight 200,000 are now commercialized by Hayashibara Shoji Co., Ltd., Okayama, Japan.

Pullulan is used in various fields such as food products, pharmaceuticals, and cosmetics because it is relatively acid- and alkali-stable, water-soluble, colorless, and odorless polysaccaride, and it has a satisfactory agglutination, adhesiveness, adhesion, stickiness, and membrane-forming properties. Furthermore, it can be easily processed into various forms of shaped products such as water-soluble filaments and colorless, transparent edible films, capsules, and tubes because of its shaping and spinning properties.

When films as examples of the shaped pullulan products are produced, various substances are usually dissolved in material aqueous pullulan solutions to improve the properties of the final products. For example, to improve the desired stability against humidity, especially the desired tolerance to dryness in shaping, glycerol and sugar alcohols are generally used. The present inventors examined in various ways and found that non-reducing saccharides composed of glucose units impart a higher level of stability against humidity to the shaped products than those attained by conventional glycerin and sugar alcohols as disclosed in Japanese Patent Application No. 129,118/2001.

In the case of producing shaped pullulan products using α,α-trehalose as non-reducing saccharides composed of glucose units, if only commercialized pullulan and α,α-trehalose products, which are usually available in a powder form, can be mixed and dissolved in appropriate solvents, the processibility would be greatly improved in actual use. However, it was revealed that such pullulan products and α,α-trehalose products would not be suitable as materials for producing shaped products because, even if they are well dispersed and mixed together, they become to be separated each other and could not keep the uniformity as a mixture of powders when received vibration during weighing, packaging, moving/transporting, and handling due to their great difference in bulk density, though they retain their powdery forms. For this reason, both the pullulan and α,α-trehalose products must be weighed each and dissolved in appropriate solvents just before use, and this hinders their handlings.

Referring to conventional pullulan products per se, they do not necessarily have a sufficient rate of water dissolution. If a greater rate of water dissolution can be imparted to such pullulan products without lowering their resistance to humidity, the workability for dissolution would be more improved.

The first object of the present invention is to provide a pullulan-containing powder that constantly retains its uniformity, does not lose its resistance to humidity, and has an improved rate of water dissolution. The second object of the present invention is to provide a process for producing the pullulan-containing powder. Further, the third object of the present invention is to provide uses of the pullulan-containing powder prepared by the process.

DISCLOSURE OF INVENTION

The present inventors eagerly studied to solve the above objects. As a result, they found that a pullulan-containing powder, which comprises pullulan and a non-reducing saccharide(s) composed of glucose units uniformly, is produced in such a manner of providing pullulan and a non-reducing saccharide(s) composed of glucose units into a homogeneous solution, drying and pulverizing the solution; and that the powder is a quite novel pullulan-containing powder does not cause separation of the ingredients, and unexpectedly has an increased rate of water dissolution without losing resistance to humidity.

Concretely speaking, for example, in preparing shaped products, the pullulan-containing powder of the present invention can be satisfactorily weighed and dissolved in appropriate solvents so that it can shorten the handling time and improve the workability compared with conventional procedures which need to weigh respectively both the material pullulan and non-reducing saccharides, composed of glucose units, and make them into solutions. Also, the pullulan-containing powder of the present invention has an improved rate of water dissolution without losing its resistance to humidity and shortens the time required for its dissolution, and it can impart a satisfactory stability against humidity change to the final shaped products.

As mentioned above, the present inventors established the pullulan-containing powder and the process thereof by providing a solution comprising pullulan and a non-reducing saccharide(s) uniformly, pulverizing the solution, and collecting the resulting powder, and they found that the objects of the present invention can be solved by providing uses such as food products, cosmetics, pharmaceuticals, and shaped products using the pullulan-containing powder. Thus, they accomplished the present invention.

EXPLANATION OF SYMBOLS

.. ■ .. Pullulan-containing powder free of non-reducing saccharide
_ ■ _ Pullulan-containing powder with trehalose
_ ■ _ Pullulan-containing powder with cyclic tetrasaccharide
.. ✕ .. Pullulan-containing powder with α-CD

BEST MODE FOR CARRYING OUT THE INVENTION

The pullulan-containing powder of the present invention includes any powder comprising pullulan and a non-reducing saccharide(s) composed of glucose units (hereinafter, may be abbreviated as "non-reducing saccharide(s) throughout the specification), preferably, those in the form of an amorphous powder having uniformity up to a level of internal powdery particles. Examples of the method for preparing solutions, containing the above pullulan and saccharide(s) uniformly, to be pulverized, are as follows: Prepare a commercialized pullulan powder and a commercialized non-reducing saccharide(s) into a solution which uniformly dissolves the saccharides, and then pulverize the solution by conventional method to obtain the pullulan-containing powder of the present invention.

The pullulan-containing powder of the present invention can be also prepared in such a manner of culturing a microorganism of the species *Aureobasidium pullulans* as a pullulan-producing microorganism in a nutrient culture medium containing non-reducing and reducing saccharides as carbon sources to produce pullulan, and subjecting the culture containing the produced pullulan and the remaining non-reducing saccharide not assimilated by the microorganism to separation of microorganism, purification, concentration, and pulverization. Also, the pullulan-containing powder can be prepared in such a manner of dissolving a non-reducing saccharide(s) in a pullulan-containing solution before completion of the purification, concentration, or pulverization of a culture medium containing pullulan obtained by culturing the above-identified microorganism in a conventional nutrient medium to produce pullulan, to obtain a homogeneous solution; and pulverizing the solution by conventional method.

Conventional pulverization methods can be appropriately selected in practicing the present invention. Examples of such are spray-drying method and a crushing method where the contents are pulverized after dried by drum dryer.

The term "a non-reducing saccharide(s) composed of glucose units" as referred to as in the present invention means a homo-oligosaccharide(s) composed of glucose units only, such as α,α-trehalose, cyclic tetrasaccharides, and cyclodextrins.

The term "α,α-trehalose" as referred to as in the present invention means a non-reducing saccharide composed of two glucose molecules bound together via the α,α-1,1 glucosidic linkage. α,α-Trehalose can be used in the present invention independently of its origin. Examples of such α,α-trehalose are those prepared by extracting from a yeast as disclosed in Japanese Patent Kokai No. 246,097/95, prepared from maltose by using a phosphorylase method as disclosed in Japanese Patent Kokai No. 216,695/83, and prepared by enzymatically saccharificating starch as disclosed in Japanese Patent Nos. 170,977/95 and 213,283/95. For example, "TREHA®", a high-purity hydrous crystalline trehalose commercialized by Hayashibara Shoji Inc., Okayama, Japan, is commercially available.

The term "a cyclic tetrasaccharide(s)" as referred to as in the present invention means a cyclic non-reducing saccharide(s) composed of four glucose units and bound alternatively with the α-1,3 and α-1,6 glucosidic linkages to form a cyclic structure, the structure of which is disclosed by Gail M. Bradbrook et al., *Carbohydrate Research*, Vol. 329, pp. 655-665 (2000). The saccharide can be easily prepared by the method disclosed in Japanese Patent Application No. 234,937/2000 by the present applicant.

The term "a cyclodextrin(s)" as referred to as in the present invention means a cyclic non-reducing saccharide(s) composed of glucoses bound together via the α-1,4 glucosidic linkage. The saccharide can be easily prepared from starch by enzymatic saccharification method using cyclodextrin glucanotransferase, and commercialized ones of which are α-, β- and γ-cyclodextrins composed of six, seven, and eight glucoses, respectively.

The content of non-reducing saccharide(s) contained in the pullulan-containing powder of the present invention varies depending on the level of non-reducing saccharides remained in the nutrient medium used in preparing pullulan and that consumed by pullulan-producing microorganisms, and/or the amount of non-reducing saccharide to be remained in the solutions up to the steps of purifying, concentrating, and pulverizing the culture medium with produced pullulan.

An excessive amount of non-reducing saccharides in the pullulan-containing powder may affect the intrinsic properties of pullulan, such as agglutination, binding, and adhesion properties. Therefore, in use, it may make the final pullulan-based shaped products such as films and capsules fragile as the demerit. While an over shortage amount of non-reducing saccharides fails to attain the effect of the present invention. In view of the properties of the pullulan-containing powder and the shaped products prepared therewith, the content of pullulan contained in the pullulan-containing products is at least 50 w/w % (hereinafter, abbreviated as "%" throughout the specification, unless specified otherwise), on a dry solid basis (d.s.b.), and the content of a non-reducing saccharide(s) to the pullulan is at least 0.1% but less than 100%, preferably, 0.5 to 60%, d.s.b.

The term "comprises uniformly" as refer to as in the present invention means that a specimen contains a substantially constant level of pullulan and a non-reducing saccharide(s) wherever sampled of the pullulan-containing powder of the present invention.

The term "a increased rate of dissolution" as referred to as in the present invention means that, comparing with conventional pullulan powders which hardly dissolve in solvents even when well dispersed therein and inevitably require a relatively long period of time for complete dissolution, a phenomenon that the time required for complete dissolution of pullulan is shortened by incorporating a non-reducing saccharide(s).

Examples of mixtures of reducing and non-reducing-saccharides, which are prepared from starch include those which are prepared by liquefying starch, subjecting the liquefied starch to the action of enzymes such as a non-reducing saccharide-forming enzyme and a trehalose-releasing enzyme disclosed in Japanese Patent Kokai No. 213,283/95; an ▪-isomaltosylglucosaccharide-forming enzyme and an ▪-isomaltosyl-transferring enzyme disclosed in Japanese Patent Kokai No. 234,937/2000 by the same applicant as the present invention; and cyclomaltodextrin glucanotransferase, where trehalose, cyclic tetrasaccharide, and cyclodextrin, which are composed of glucose units, are respectively formed, along with reducing oligosaccharides such as glucose and maltose, to form a saccharified solution, and optionally it can be further treated with enzymes such as glucoamylase to decompose reducing maltooligosaccharides coexisting in the saccharified solution into glucose molecules.

Saccharide solutions as mother solutions free from saccharides can be used in the present invention, where the saccharide solutions can be prepared in a conventional manner by desalting, desalting, decoloring and purifying saccharified solutions obtained using non-reducing saccharide-forming enzymes, and sequentially concentrating the resulting mixtures and crystallizing the saccharides from the concentrates by the addition of seed; or prepared by subjecting saccharified solutions containing non-reducing saccharides after desalting, decoloration and purification to chromatography using strong-acid cation exchange resins to increase the content of non-reducing saccharides, crystallizing the saccharides from the resulting mixtures by the addition of seed, and centrifuging the resulting saccharide mixtures to remove crystals.

Examples of the saccharide mixtures containing reducing and non-reducing saccharides usable in the present invention are those which comprise one or more glucose and maltooligosaccharides such as maltose, isomaltose, which are produced by hydrolyzing starch using various methods and sequentially desalting, decoloring and purifying the hydrolyzates; and those which are mixtures of commercialized saccharifed starch hydrolyzates such as glucose and starch syrup, fructose, sucrose, and blackstrap molasses, in combination with non-reducing saccharides composed of glucose units such as $\alpha,\alpha$-trehalose, cyclic tetrasaccharides, and cyclodextrins. The above saccharide mixtures can be advantageously used as carbon sources for liquid media and feeding media before and during the culture of pullulan-producing microorganisms when used as nutrient culture media.

The term "steps for purification and concentration until pulverization" as referred to as in the present invention means those where the contents are in a solution form at any step of from the termination of culturing for producing pullulan to the initiation of pulverizing pullulan solutions.

The pullulan-containing powder of the present invention, which is obtainable by providing solutions containing pullulan and non-reducing saccharides uniformly, and pulverizing the solutions by conventional methods, comprises pullulan and non-reducing saccharides in a constant proportion and has no fear of causing separation thereof. It can greatly improve the workability of preparing material solutions for producing shaped products, etc., because the pullulan-containing powder substantially does not lose resistance to humidity and has a relatively higher rate of water dissolution compared with conventional pullulan powders free of any non-reducing saccharides. Due to the non-reducing saccharides contained in the pullulan-containing powder, satisfactory stability against humidity change is imparted to the shaped products prepared with the powder as a material.

In addition to pullulan, other non-reducing saccharides such as $\alpha,\alpha$-trehalose, cyclic-tetra-saccharides, and cyclodextrins contained in the pullulan-containing powder effectively protect and stabilize substances susceptible to oxidation or volatilization as merit. Particularly, cyclic-saccharides having a hydrophobic hole intramolecularly, such as cyclic-tetrasaccharides and cyclodextrins, have the function of enclosing and stabilizing materials, i.e., an enclosing function; whereby substances susceptible to oxidation, heat/light-decomposition, and volatilization can be stabilized. The cyclic-saccharides musk smell and solubilize hardly or substantially insoluble substances, and this feature can be effectively exerted in the fields of food products, pharmaceuticals, cosmetics, and others. Since such an effect can be exerted in the shaped products prepared therewith, the pullulan-containing powder comprising cyclic saccharides of the present invention can be advantageously used as materials for producing films, capsules, etc The term "compositions comprising the pullulan-containing powder and other ingredients" as referred to as in the present invention means compositions into which the pullulan-containing powder is incorporated as a constituent to impart the potentials of pullulan such as agglutination, binding, adhesion, sticking, membrane-forming, shaping, and spinning properties; as well as to impart stability against humidity change and to stabilize and inhibit the other ingredients from volatilizing.

The lower the content of the pullulan-containing powder to the other ingredients, the lesser the above-identified features become to be expected, while the higher the content of the pullulan-containing powder to the other ingredients, the more it causes the following demerits: It increases the viscosity of the final compositions and their materials and intermediates, when they are prepared into a solution form, or affects processibility or deteriorates the properties of the final products. From these, the pullulan-containing powder is preferably added to the other materials in an amount of ranging from at least 0.5% but less than 90%, preferably, from 1 to 80%, d.s.b.

Examples of the compositions according to the present invention include food products such as confectioneries such as bread prepared with wheat flour and cleaned rice powder such as a rice paste power; lactic acid beverages; jellies; liquid foods; viscous beverages; seasonings; processed foods such as seasoned layers and delicacies; and their materials and intermediates; cosmetics such as lotions, creams, shampoos, rinses, treatments, and lip sticks, and their materials and intermediates; tooth pastes; pharmaceuticals such as sugar-coated tablets, ointments, cataplasms, and their materials and intermediates; and shaped products such as films, capsules, sheets, and strings, which are mainly composed of the pullulan-containing powder of the present invention.

Based on the above properties, the pullulan-containing powder of the present invention can be advantageously used as an excipient/filler for shaped products such as pullulan films/capsules or tablets, coating agent, stabilizer for constituents, viscosity-imparting agents for liquid products, solidifying/adhesive agent for producing solid products for use in food products, pharmaceuticals, and cosmetics.

Pullulan films, a kind of shaped product, can be heat-sealed directly, or optionally sealed after their surfaces are humidified. If necessary, in preparing pullulan films, adequate amounts of an elastic agent such as glycerin and sugar alcohols can more improve the heat-sealing property when used in combination with the pullulan-containing powder of the present invention.

The following Experiments concretely explain both a pullulan film in detail as a preferred example of the shaped products of the present invention and the properties of the pullulan-containing powder as a material of the film.

Experiment 1

Moisture Retainability and Hygroscopicity of Pullulan Film

The moisture retainability and hygroscopicity of pullulan films were examined as follows: As material solutions for preparing pullulan films, the following solutions with the ingredients as indicated below were prepared by completely dissolving in 34 g ion-exchange water 10 g of a pullulan powder, d.s.b., 0.01 g of sucrose monoraurate as a desquamation agent, and one gram of a prescribed additive(s), d.s.b., with the proviso that ion-exchange water was used for a system with no saccharide. Among the saccharides used, the following were used: Glycerin, glucose, and sucrose, which were in a reagent grade and commercialized by Wako Pure Chemicals Co., Ltd., Tokyo, Japan; maltose, maltitol, $\alpha$-cyclodextrin (hereinafter, "$\alpha$-cyclodextrin" may be abbreviated as "$\alpha$-CD"), which were reagents produced by Hayashibara Biochemical Laboratories Inc., Okayama, Japan; "TREHA®", an $\alpha,\alpha$-trehalose commercialized by Hayashibara Shoji Co., Ltd., Okayama, Japan; "PULLULAN PI-20™", a pullulan product commercialized by Hayashibara Shoji Co., Ltd., Okayama, Japan; and a cyclic-tetrasaccharide with a purity of 99.5% prepared from starch in accordance with the methods described in Examples A-3 and A-5 in Japanese Patent Application No. 234,937/2000 applied for by the same applicant as the present invention.

The material aqueous solutions for pullulan films thus prepared were deaerated in vacuo and stored in 60" hot water until actual use. The aqueous solutions were respectively poured over a synthetic plastic film to give a 150 mm in width, 500 mm in length, and 175 µm in thickness using YBA-type baker applicator commercialized by Yoshimitsu Seiki Co., Ltd., Tokyo, Japan. The applied solutions were dried uniformly using an air-dryer until the moisture content of the forming films reached a constant level. After completion of drying, the formed pullulan films were detached from the plastic films, placed in plastic bags, and sealed for preservation until use. The average thickness of the resultant pullulan films was 29±2 μm.

The shaped products were evaluated about stability to humidity change and solubility as indicated below:

Tests for moisture-retainability and hygroscopicity were carried out in a temperature-controlled room at 25°. In the tests, the samples were allowed to stand under a relative humidity (RH) of 52.8% up to reach an equilibrium state, which gave a standard weight of each pullulan film, and then transferred to a relatively low or high moisture condition and allowed to stand therein, followed by determining the reduced weight from the standard weight for each pullulan film and calculating the moisture level (%) released from or absorbed by each pullulan film based on the standard weight of each pullulan film. The formula is indicated below, where plus and minus values mean the pullulan films tested released- or absorbed-moisture, respectively.

The value $(\%) = [(S - X)/S] \times 100$  Formula:

S: Standard weight of a pullulan film,
X: Weight of a pullulan film after preservation.

Humidity-controlled desiccators, equilibrated at RH 33.0% using an aqueous solution saturated with magnesium chloride, RH 52.8% using an aqueous solution saturated with magnesium nitrate, and RH 80.7% using an aqueous solution saturated with potassium bromide, were used in the tests. Samples for testing were placed in open aluminum vessels and preserved in the desiccators.

The moisture-retainability of pullulan films was defined as properties that it showed a relatively low moisture-releasing ability, i.e., a relatively low in released-moisture, even when preserved under a relatively low humidity condition, it did not cause any change in appearance and any crack by drying, and it did not become to be fragile. The moisture-retaining ability was determined in such a manner that the pullulan films, pre-equilibrated in desiccators with RH 52.8%, were transferred and preserved in desiccators with RH 33.0% for 48 hours, and the amount of moisture released from the pullulan films were weighed at regular time intervals, and also the change of their appearance was observed. The denotation, "Yes", for moisture-retaining ability means that the pullulan films did not or did not substantially show any change in appearance and elasticity due to fragility. The denotation, "No", means that the pullulan films showed an apparent change in shape and reduction of elasticity due to fragility.

The elasticity of pullulan films was judged by the criterion whether the films were cracked/broken or not by repeatedly bending and stretching them at an angle of 180° to the same direction. The denotation, "Yes", means that the films were not cracked by five times of the above bending and stretching. The denotation, "No", means that the films were broken by a single bending and stretching. The denotation, "F (fragile)" means that the films were judged to have an intermediate property between the above "Yes" and "No".

The resistance to humidity of pullulan films was defined as that, even when allowed to stand at a relatively high moisture condition, the films gave a relatively low moisture-absorbability in terms of the level of absorbed moisture or had a lesser change in the appearance and the surface of the films, as well as in the aspects of adhesion and melting induced by moisture absorption, even though the films absorbed moisture to some extent. The resistance to humidity was determined in such a manner that the pullulan films, pre-equilibrated in a desiccator with RH 52.8%, were transferred to and preserved in a desiccator with RH 80.7% for 48 hours, the amount of moisture absorbed by the pullulan films was determined based on the weight change at regular intervals, and the change in appearance was also observed. The denotation, "Yes" in terms of the resistance to humidity, means that, even though the films absorbed-moisture to some extent after standing in a desiccator with RH 80.7% for 48 hours, they showed a little or no change in appearance and surface, and gave a little or no adhesibility. The denotation, "No", in terms of the resistance to humidity, means that the films showed a change in shape and surface and induced adhesibility.

The adhesion of pullulan films was tested by piling pullulan films, as samples, in aluminum vessels, allowing them to stand therein for 48 hours, taking out the films of the vessels, and observing the properties, etc., of the resultant films; and the results were judged based on the following five grades of criterion:

A: The films melted, lost their inherent shapes, and tightly adhered to the aluminum vessels;
B: The films strongly adhered each other and to the aluminum vessels;
C: The films adhered each other and to the vessel, but they were easily detachable.
D: The films loosely adhered each other but not adhered to the aluminum vessels; and
E: No adhesion was observed.

Table 1 is the results of the tests on moisture-retainability and moisture-absorbability of the pullulan films obtained in this experiment.

TABLE 1

| | Moisture-retaining test | | | Moisture-absorbing test | | |
|---|---|---|---|---|---|---|
| Additives | Released moisture percentage (%) | Elasticity | Judgement | Absorbed moisture percentage (%) | Adhesibility | Judgement |
| Glycerin | 2.18 | F | No | 13.67 | B | No |
| Glucose | 1.94 | F | No | 9.95 | D | No |
| Maltose | 1.89 | F | No | 9.84 | D | No |
| Sucrose | 2.04 | F | No | 9.55 | D | No |
| α,α-Trehalose | 1.78 | Yes | Yes | 9.40 | E | Yes |
| Maltitol | 1.79 | Yes | Yes | 10.66 | C | No |
| Cyclic tetrasaccharide | 1.83 | Yes | Yes | 9.47 | E | Yes |
| α-CD | 1.86 | Yes | Yes | 9.57 | E | Yes |
| None (Only water) | 2.32 | No | No | 7.92 | E | Yes |

The results from the moisture-retaining test showed the pullulan film with no addition of saccharide gave a high level of moisture release to lose moisture content and to be dried, fragile, and broken. While, all the pullulan films prepared with saccharides less released moisture, particularly, those with maltose, α,α-trehalose, maltitol, cyclic tetrasaccharide, or α-CD showed a lesser level of released-moisture. Regarding the elasticity of pullulan films, those with α,α-trehalose, maltitol, cyclic tetrasaccharide, or α-CD retained a satisfactory elasticity, but those with glycerin, glucose, maltose, or sucrose were easily fragile.

The results from the moisture-absorbing test, conducted at a relatively high humidity, showed that the pullulan film with no addition of saccharide was stable due to the lowest level of absorbed moisture. In contrast, all the pullulan films prepared with saccharides absorbed moisture, particularly, those with glycerin or maltitol showed a higher level of moisture absorption. Regarding the adhesibility of the pullulan films, since those with α,α-trehalose, cyclic tetrasaccharide, or α-CD and that with no addition of saccharide gave no adhesion, they were judged satisfactory, but that with glycerin showed an unsatisfactory strong adhesion.

Considering the above results totally, it was revealed that non-reducing saccharides composed of glucose units, such as α,α-trehalose, cyclic tetrasaccharide, and α-CD, more effectively impart the desired stability to humidity change, i.e., moisture-retainability and absorbability, than those conventionally used glycerin and maltitol.

Experiment 2
Preparation and Property of Pullulan-Containing Powder with Non-Reducing Saccharide and Preparation of Films Therewith Experiment 2-1
Preparation of Pullulan-Containing Powder with α,α-trehalose, Cyclic Tetrasaccharide, or α-CD Pullulan-containing powders with α,α-trehalose, cyclic tetrasaccharide, or α-CD were prepared using "Pullulan PI-20™", a pullulan commercialized by Hayashibara Shoji Co., Ltd., Okayama, Japan, and "TREHA®"; an α,α-trehalose commercialized by Hayashibara Shoji Co., Ltd., Okayama, Japan; 99.5% purity of a cyclic tetrasaccharide prepared in Experiment 1; and α-CD produced by Hayashibara Biochemical Laboratories, Inc., Okayama, Japan. After quantifying the pullulan content in Pullulan PI-20™ by the later described method using pullulanase, a prescribed volume of pullulan solution was prepared and admixed with 10.0%, d.s.b., of either of the non-reducing saccharides to the content of pullulan in the solution, followed by dissolving the saccharides into solutions which dissolved pullulan and either of the non-reducing saccharides.

The resulting solutions were concentrated into about 35% solutions using an evaporator, transferred stainless-steel butts with a synthetic plastic film spread over, and dried in vacuo—at 30° C. for two days to obtain dried products. The resulting dried products were pulverized by a grinder mill, a power mill with round screening pores of 1.5 mm in diameter, to obtain pullulan-containing powders with non-reducing saccharides as examples of the present invention. As a control, a pullulan-containing powder with non-non-reducing saccharide was prepared similarly as above.

The contents of pullulan and non-reducing saccharides were measured as follows: Two hundred milligrams of a sample was dissolved in 0.05M acetate buffer (pH 6.0), admixed with 200 units of a commercialized pullulanase, produced by Hayashibara Biochemical Laboratories Inc., Okayama, Japan, to completely hydrolyze pullulan into maltotriose units. The resulting solution was concentrated in vacuo into an about 1.5% saccharide solution, followed by filtering it with "MILLEX-HV", a cartridge filter with 0.45 μm in pore size and 13 mm in diameter, produced by Nihon Millipore Corporation, Tokyo, Japan. The resulting solution was desalted by "MICROACYLIZER GO, TYPE AC-110-04", an electrodialysis device produced by Asahi Kasei Corporation, Tokyo, Japan. The desalted solution was subjected to liquid chromatography using "CK04SS", a column produced by MCI Co., Ltd., Tokyo, Japan, or "SHODEX KS-801", a column produced by Showa Denko Co., Ltd., Tokyo, Japan. Based on the ratios of the detected peak areas corresponding to each saccharide, the percentage of saccharides was calculated. The content of pullulan was determined based on the amount of maltotriose formed by the action of pullulanase.

Percentage of pullulan to total saccharides in pullulan-containing powder (%)=(P/T)×100

Percentage of α,α-trehalose, cyclic tetrasaccharide, or α-CD to pullulan in pullulan-containing powder (%)=(S/P)×100

In the above Formulae:
P: Peak area corresponding to maltotriose formed by the action of pullulanase
T: Total sum of all the peak areas corresponding to saccharides
S: Peak area corresponding to α,α-trehalose, cyclic tetrasaccharide, or α-CD Table 2 is the results of componental analysis of pullulan-containing powder.

TABLE 2

| Added saccharide | Standard weight (g) | Moisture content (%) | Non-reducing saccharide/ Pullulan (%) | Pullulan/ Total saccharides (%) |
|---|---|---|---|---|
| None | 266 | 0.6 | 0.0 | 97.8 |
| α,α-Trehalose | 274 | 0.6 | 10.0 | 89.0 |
| Cyclic-Tetrasaccharide | 269 | 0.6 | 10.0 | 89.0 |
| α-CD | 258 | 0.6 | 10.0 | 89.0 |

"PULLULAN PI-20™", a commercialized pullulan product, used for preparing pullulan-containing powders as examples of the present invention, contained a small amount of 2.3% of reducing saccharides other than pullulan. The pullulan-containing powders contained 10%, d.s.b., of the non-reducing saccharides to the amount of pullulan similarly as in the initiation of their preparations.

Experiment 2-2
Test on Uniformity of Pullulan-Containing Powder

To test the uniformity of pullulan-containing powders, as a control, according to conventional method of mixing different powders, a pullulan-containing powder free of non-reducing saccharide and a powder of non-reducing saccharide were mixed to homogeneity to obtain a mixed powder. In detail, the mixed powder was prepared by adding 10.0%, d.s.b., of a α,α-trehalose crystalline powder, cyclic-tetrasaccharide crystalline powder, or α-CD crystalline powder to the pullulan powder free of non-reducing saccharide in Experiment 2-1, and mixing the powders to homogeneity.

The grain size of the above non-reducing saccharides was not particularly adjusted to that of the pullulan-containing powder free of non-reducing saccharide, prepared in Experiment 2-1.

Three gram aliquots of the pullulan-containing powders of the present invention and of the mixed powders, prepared by the above-identified conventional method, were respectively placed in a 10-ml volume of plastic test-tube with a cap, vibrated in such a manner of dropping the test tubes carefully on a table from the height of about 20 cm over the table 10 or 20 times (tapping treatment), and sampling 200 mg powder from each test tube at the point of 1 cm from the upper or the bottom side of the tube. The samples were analyzed for percentage of a non-reducing saccharide to pullulan to investigate the uniformity of the contents. In detail, the proportion of a non-reducing saccharide to pullulan was calculated based on the peak areas corresponding to the saccharides determined on chromatograms after the samples were treated similarly as in Experiment 2-1. Table 3 is the results of the uniformity test for the pullulan-containing powders and the mixed powders.

Experiment 2-3
Solubility

The solubility test on samples was carried out using the following two methods:

(1) Three grams of any one of the pullulan-containing powders was placed in a 500-ml beaker set on a stirrer, followed by sequentially pouring 300 ml of 50° C. ion-exchange water on the powder, simultaneously starting to stir the mixture at a constant rotation rate of 250 rpm, and measuring the time required for completely dissolving the powder.

(2) Five hundred milliliters of 50° C. ion-exchange water was placed in 500-ml beaker, and 100 mg of any one of the pullulan-containing powders was uniformly spread over the water surface, followed measuring the time required for completely dissolving the powder.

TABLE 3

| Preparation of powder | Ingredient | Separation and treatment | Sampling position | Trehalose/ Pullulan (%) |
|---|---|---|---|---|
| Powder obtained by pulverizing solution | Pullulan-containing powder with α,α-trehalose | Just after preparation | | 10.0 |
| | | 10 times of tapping | Upper | 10.0 |
| | | | Bottom | 10.0 |
| | | 20 times of tapping | Upper | 10.0 |
| | | | Bottom | 10.0 |
| | Pullulan-containing powder with cyclic tetrasaccharide | Just after preparation | | 10.0 |
| | | 10 times of tapping | Upper | 10.0 |
| | | | Bottom | 10.0 |
| | | 20 times of tapping | Upper | 10.0 |
| | | | Bottom | 10.0 |
| | Pullulan-containing powder with α-CD | Just after preparation | | 10.0 |
| | | 10 times of tapping | Upper | 10.0 |
| | | | Bottom | 10.0 |
| | | 20 times of tapping | Upper | 10.0 |
| | | | Bottom | 10.0 |
| Powder obtained by mixing different powders | Mixed powder of a pullulan powder consisting of pullulan- and a α,α-trehalose crystalline powder | Just after preparation | | 10.0 |
| | | 10 times of tapping | Upper | 9.2 |
| | | | Bottom | 12.2 |
| | | 20 times of tapping | Upper | 7.3 |
| | | | Bottom | 14.8 |
| | Mixed powder of a pullulan powder consisting of pullulan and a cyclic tetrasaccharide crystalline powder | Just after preparation | | 10.0 |
| | | 10 times of tapping | Upper | 9.4 |
| | | | Bottom | 11.8 |
| | | 20 times of tapping | Upper | 7.6 |
| | | | Bottom | 13.7 |
| | Mixed powder of a pullulan-powder consisting of pullulan and an α-CD crystalline powder | Just after preparation | | 10.0 |
| | | 10 times of tapping | Upper | 8.9 |
| | | | Bottom | 12.7 |
| | | 20 times of tapping | Upper | 8.3 |
| | | | The bottom | 13.1 |

The mixed powders, prepared by mixing a pullulan-containing powder free of non-reducing saccharide and any of the α,α-trehalose crystalline powder, cyclic tetrasaccharide crystalline powder, and ˝-CD crystalline powder, were roughly uniformly just after preparation, but they could not keep the uniformity as the increase of the times of tapping because they gave a significant difference between the percentages (%) of pullulan and α,α-trehalose, cyclic tetrasaccharide, or α-CD. While, the pullulan-containing powders of the present invention, which were prepared by dissolving pullulan together with α,α-trehalose, cyclic tetrasaccharide, or α-CD in a solvent into homogeneous solutions, and pulverizing the solutions, constantly kept the percentage of pullulan and α,α-trehalose, cyclic tetrasaccharide, or α-CD, meaning that they kept the desired uniformity.

Table 4 is the results on the solubility test for the pullulan-containing powders.

TABLE 4

| Dissolution method | Added ingredient | Dissolving status |
|---|---|---|
| Pouring 50° C. hot water on a test powder and instantly mixing the mixture | None | Absorbing water in 1.25 min and completely dissolving in 2 min |
| | α,α-Trehalose | Absorbing water in 53 sec and completely dissolving in 1 min and 9 sec. |
| | Cyclic tetrasaccharide | Absorbing water in 56 sec and completely |

TABLE 4-continued

| Dissolution method | Added ingredient | Dissolving status |
|---|---|---|
| | α-CD | dissolving in 1 min and 12 sec. Absorbing water in 47 sec and completely dissolving in 1 min and 8 sec. |
| Dispersing a test powder over 50° C. hot water with no stirring and allowing the mixture to stand | None | Absorbing water completely in 9 min and roughly dissolving in 12 min. |
| | α,α-Trehalose | Absorbing water completely in 6 min and roughly dissolving in 8 min. |
| | Cyclic tetrasaccharide | Absorbing water completely in 7 min and dissolving in 9 min. |
| | α-CD | Absorbing water completely in 5 min and dissolving in 7 min. |

From the results of the solubility test, the pullulan-containing powders with any of α,α-trehalose, cyclic-tetrasaccharide, or α-CD gave a higher rate of water dissolution in both dissolution methods and dissolved in a shorter period of time than those with pullulan-containing powder free of non-reducing saccharide.

Experiment 2-4
Moisture-Absorbing Test for Pullulan-Containing Powder

Figure 1:
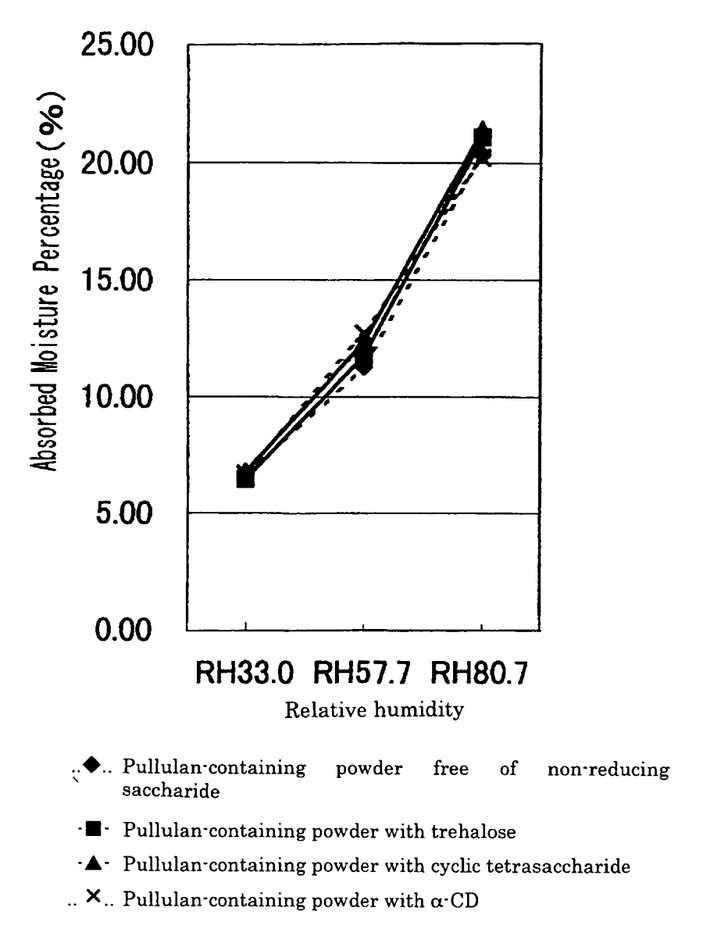
FIG. 1 shows the results of the moisture-absorbing test for pullulan-containing powders.

Moisture-absorbing test for pullulan-containing powder was carried out as follows: After dried in vacuo for 12 hours at ambient temperature, three gram aliquots of the resulting test samples precisely weighed and placed in aluminum vessels. To saturate the moisture content, the test samples were allowed to stand for two days without sealing the vessels with caps in a desiccator with RH 33.0% equilibrated with an aqueous solution saturated with magnesium chloride, RH 57.7% equilibrated with an aqueous solution saturated with sodium chloride, or with RH 80.7% equilibrated with an aqueous solution saturated with potassium bromide. Thereafter, the aluminum vessels were taken out from the desiccators, weighed, and observed about the property changes of the test samples in the vessels, such as adhesion to the vessels, aggregation of powders, and loss of volume. The level of absorbed moisture was determined by measuring the increased weight of the test samples after absorbing moisture during storage and calculating with the formula described in Experiment 2-1. FIG. 1 shows the results of this moisture-absorbing test.

As evident from the results in FIG. 1, all the pullulan-containing powder with α,α-trehalose, cyclic tetrasaccharide, or α-CD showed the same pattern of moisture increase compared with the pullulan-containing powder with no non-reducing saccharide. Regarding the properties of the pullulan-containing powders during the storage period in the moisture-absorbing test, they did not show any change in the properties of adhesion to aluminum vessels, aggregation of powders, and bulk decrease of the powders compared with the pullulan-containing powder with no non-reducing saccharide. From these results, it was revealed that the pullulan-containing powders of the present invention did not lose resistance to humidity compared with the pullulan-containing powder with no non-reducing saccharide as a control.

Experiment 2-5
Preparation and Test on Physical Property of Pullulan Film

Preparation and test on physical property of pullulan films were carried out as follows: The solutions with the following compositions were used as material aqueous solutions to prepare pullulan films and prepared by mixing 10 g, d.s.b., of the pullulan-containing powder free of α,α-trehalose in Experiment 2-1, 0.01 g of sucrose monoraurate as a remover, and 0.5 g, 1.0 g, 1.5 g, or 2.0 g of glycerin, and completely dissolving the resulting mixture in 34 g of ion-exchange water; or by mixing 11 g, d.s.b., of the pullulan-containing powder free of α,α-trehalose in Experiment 2-1, 0.01 g of sucrose monoraurate as a remover, and 0.5 g, 1.0 g, 1.5 g, or 2.0 g of glycerin, and completely dissolving the resulting mixture in 33 g of ion-exchange water. The above material aqueous solutions were deaerated in vacuo and stored in 60 ° hot water before use.

The material solutions were respectively poured over a synthetic plastic film with a 150 mm in width, 500 mm in length, and 175 μm in thickness using a YBA-type baker applicator commercialized by Yoshimitsu Seiki Co., Ltd., Tokyo, Japan, and dried uniformly using an air-dryer until they gave a moisture content of 7.5%. After drying, the resulting pullulan films were detached from the synthetic plastic films, placed in vinyl bags, and stored after sealing the bags. The pullulan films thus obtained had a thickness of 28±2 μm.

Moisture-retaining test and moisture-absorbing test were carried out according to the methods in Experiment 1, and the results were evaluated similarly as above.

The heat-seal property test was carried as follows: The pullulan films were heat-sealed by pressing at 1.5 kg/cm² using "TYPE FA-300" commercialized by Fuji Impuls Co., Ltd., Shizuoka, Japan, preserved in vinyl bags at ambient temperature for two days, and observed the heat-sealed conditions. When the pullulan films were heat-sealed, they were moistened at their sealing parts with steam (hereinafter, this treatment is abbreviated as "moisture-control" in the specification). As the criterion for heat-sealing property, the denotations of "No" and "Yes" mean that it was easily detached and it could not be detached, respectively, when both sides of the heat-sealed parts were pulled by hands rather strongly.

Table 5 is the results of the test on heat-sealing, the moisture-retainability, and the moisture-absorbability of the pullulan films tested.

TABLE 5

| Percentage (%)* | | Test on moisture-retainability | | | Test on moisture-absorbability | | | Test on heat-sealing | |
|---|---|---|---|---|---|---|---|---|---|
| α,α-Trehalose | Glycerin | Released moisture (%) | Elasticity | Judgement | Absorbed moisture (%) | Adhesibility | Judgement | With no moisture control | With moisture control |
| 0 | 0 | 2.32 | F | No | 7.92 | E | Yes | No | Yes |
| | 5 | 2.25 | F | No | 9.45 | E | Yes | Yes | Yes |
| | 10 | 2.18 | F | No | 13.67 | B | No | Yes | Yes |
| | 15 | 2.04 | F | No | 15.18 | B | No | Yes | Yes |

TABLE 5-continued

| Percentage (%)* | | Test on moisture-retainability | | | Test on moisture-absorbability | | | Test on heat-sealing | |
|---|---|---|---|---|---|---|---|---|---|
| α,α-Trehalose | Glycerin | Released moisture (%) | Elasticity | Judgement | Absorbed moisture (%) | Adhesibility | Judgement | With no moisture control | With moisture control |
| 10 | 0 | 1.78 | Yes | Yes | 9.40 | E | Yes | No | Yes |
|  | 0.5 | 1.76 | Yes | Yes | 9.49 | E | Yes | Yes | Yes |
|  | 1 | 1.74 | Yes | Yes | 9.54 | E | Yes | Yes | Yes |
|  | 1.5 | 1.72 | Yes | Yes | 9.65 | D | No | Yes | Yes |

Note:
Percentages to the weight of pullulan, d.s.b.

When the content of glycerin is low, the pullulan films, which were prepared by using aqueous solutions containing pullulan and glycerin, released a relatively large amount of moisture in the test on moisture retainability to lower their water content, resulting in being dried, fragile, and easily broken. From the results of the test on moisture-absorbability, the more the amount of glycerin in the pullulan films, the more the films became to show a relatively strong adhesion.

In the test on moisture retainability, the pullulan films, prepared by using aqueous solutions with pullulan, glycerin, and α,α-trehalose, showed an inhibited moisture release due to the incorporated α,α-trehalose, lesser reduction of moisture level, and satisfactory elasticity in spite of a lesser amount of glycerin. From the results of the test on moisture absorbability, the incorporated α,α-trehalose inhibited moisture absorption and did not substantially exhibit adhesion in spite of a larger amount of glycerin.

From the results of the test on heat sealing, the pullulan films with no glycerin showed an incomplete adhesion when the surfaces of the films were not controlled. While, the pullulan films, which had been moistened their surfaces and/or contained adequate amounts of glycerin, were satisfactorily heat-sealed independently of the presence of α,α-trehalose.

These results of the tests revealed that pullulan-containing powders with α,α-trehalose facilitate to produce film compositions having an imparted stability against moisture change, and that, when glycerin is coexisted, such powders effectively counteract the undesirable affects of glycerin by the effects of α,α-trehalose contained therein.

Based on the above results, the pullulan-containing powders, comprising non-reducing saccharides according to the present invention, comprise pullulan and a non-reducing saccharide(s) uniformly in a prescribed ratio, and have no fear of causing separation of the ingredients. Comparing with conventional pullulan powders with no non-reducing saccharide, the pullulan-containing powders of the present invention do not substantially lose their satisfactory resistance to moisture, and have a greater rate of water dissolution. Further, the pullulan-containing powders of the present invention improve the processibility of material solutions for shaped products by a large margin, and impart stability against humidity change to the final products produced from the powders as a material.

The present invention is concretely explained with reference to the following preferred embodiments according to the present invention but not limited thereby:

Example A-1

Pullulan-Containing Powder with α,α-trehalose

In accordance with the method in Example A-6 of Japanese Patent Kokai No. 156,338/93, liquefied starch was subjected to the action of a non-reducing saccharide-forming enzyme, trehalose-releasing enzyme, starch blanching enzyme, etc., to produce a saccharified solution with 80% α,α-trehalose, d.s.b. A pullulan-producing microorganism of the species *Aureobasidium pullulans* was cultured in a liquid nutrient culture medium containing 10% of the above saccharified solution as a carbon source. After completion of the culture, a pullulan-containing powder with α,α-trehalose as a non-reducing saccharide was obtained from the resultant culture in a conventional manner through the techniques of filtration for removing microorganisms, purification and decolorization with activated carbons, desalting and purification using ion-exchange resins, concentration, drying, and pulverization. The pullulan-containing powder thus obtained contained 69.2% of pullulan, 21.3% of α,α-trehalose, 6.2% of glucose, and 3.3% of other oligosaccharides. The percentage of α,α-trehalose to pullulan was 30.8%, d.s.b.

The product contains pullulan and α,α-trehalose uniformly with less fear of causing separation of the ingredients, does not lose resistance to humidity, and has a satisfactory rate of water dissolution. Accordingly, the product can be suitably used as a material for food products, cosmetics, and pharmaceuticals, particularly, films, capsules, etc., because the product imparts stability against humidity change to the shaped products.

Example A-2

Pullulan-Containing Powder with α,α-trehalose

In accordance with the method in Example A-1, a saccharified solution containing 85% of α,α-trehalose, d.s.b., which had been prepared by subjecting liquefied starch to the action of a non-reducing saccharide-forming enzyme, trehalose-releasing enzyme, starch debranching enzyme, etc., was purified, concentrated, and crystallized by adding a seed crystal, to obtain a solution containing crystalline α,α-trehalose. The solution thus obtained was centrifuged to collect the produced hydrous crystalline α,α-trehalose and to obtain a mother liquor containing 15% of α,α-trehalose, d.s.b. Similarly as in Example A-1, a pullulan-producing microorganism of the species *Aureobasidium pullulans* was cultured in a liquid nutrient culture medium containing 10% of the above saccharide solution as a carbon source. After completion of the culture, a pullulan-containing powder with α,α-trehalose as a non-reducing saccharide was obtained from the resultant culture in a conventional manner through the techniques of filtration for removing microorganisms, purification and decolorization with activated carbons, desalting and purification using ion-exchange resins, concentration, drying, and pulverization. The pullulan-containing powder thus obtained contained 90.5% of pullulan, 2.7% of α,α-trehalose, 2.3% of glucose, and 4.5% of other oligosaccharides. The percentage of α,α-trehalose to pullulan was 3.0%, d.s.b.

The product contains pullulan and α,α-trehalose uniformly with less fear of causing separation of the ingredients, does not lose resistance to humidity, and has a satisfactory rate of water dissolution. Accordingly, the product can be suitably used as a material for food products, cosmetics, and pharmaceuticals, particularly, films, capsules, etc., because the shaped product imparts stability against humidity change to the shaped products.

Example A-3

Pullulan-Containing Powder with α,α-trehalose

Similarly, as in Example A-1, using a nutrient culture medium containing 10% of a commercialized starch hydrolyzate as a carbon source, a pullulan producing microorganism of the species *Aureobasidium pullulans* was cultured. After completion of the culture, the resulting culture was in a conventional manner subjected to filtration for removing microorganisms, purification and decolorization with activated carbons, and desalting and purification using ion-exchange resins. To the pullulan-containing solution thus obtained was added and dissolved therein "TREHA®" commercialized by Hayashibara Shoji Co., Ltd., Okayama, Japan, in an amount of 14.5%, d.s.b., to the total sugars in the solution. The resulting mixture was mixed to homogeneity, concentrated, dried and pulverized to obtain a pullulan-containing powder with α,α-trehalose as a non-reducing saccharide. The pullulan-containing powder thus obtained contained 84.7% of pullulan, 12.6% of α,α-trehalose, 1.3% of glucose, and 1.4% of other oligosaccharides. The percentage of α,α-trehalose to pullulan was 14.9%, d.s.b.

The product contains pullulan and α,α-trehalose uniformly with less fear of causing separation of the ingredients, does not lose resistance to humidity, and has a satisfactory rate of water dissolution. Accordingly, the product can be suitably used as a material for food products, cosmetics, and pharmaceuticals, particularly, films, capsules, etc., because the product imparts stability against humidity change of the shaped products.

Example A-4

Pullulan-Containing Powder with α-cyclodextrin

Similarly as in Example A-1, a pullulan producing microorganism of the species *Aureobasidium pullulans* was cultured in a nutrient culture medium containing 10% of a commercialized starch hydrolyzate as a carbon source. After completion of the culture, the resulting culture was in a conventional manner subjected to filtration for removing microorganisms, purification and decolorization with activated carbons. To the pullulan-containing solution thus obtained was added and dissolved therein α-cyclodextrin commercialized by Hayashibara Shoji Co., Ltd., Okayama, Japan, in an amount of 14.5%, d.s.b., to the total sugars in the solution. The resulting mixture was mixed to homogeneity, concentrated, dried and pulverized to obtain a pullulan-containing powder with α-cyclodextrin as a non-reducing saccharide. The pullulan-containing powder thus obtained contained 85.1% of pullulan, 12.8% of α-cyclodextrin, 1.1% of glucose, and 1.0% of other oligosaccharides. The percentage of α-cyclodextrin to pullulan was 15.0%, d.s.b.

The product contains pullulan and α-cyclodextrin uniformly with less fear of causing separation of the ingredients, does not lose resistance to humidity, and has a satisfactory rate of water dissolution. Accordingly, the product can be suitably used as a material for food products, cosmetics, and pharmaceuticals, particularly, since the product contains α-cyclodextrin, it can be suitable used in compositions which comprise ingredients susceptible to oxidation, thermal decomposition, light decomposition, etc., or other volatile ingredients.

Example A-5

Pullulan-Containing Powder with α-cyclodextrin

Similarly as in Example A-1, a pullulan producing microorganism of the species *Aureobasidium pullulans* was cultured in a nutrient culture medium containing 10% of a commercialized starch hydrolyzate as a carbon source. After completion of the culture, the resulting culture was in a conventional manner subjected to filtration for removing microorganisms, purification and decolorization with activated carbons. To the pullulan-containing solution thus obtained was added and dissolved therein β-cyclodextrin commercialized by Hayashibara Shoji Co., Ltd., Okayama, Japan, in an amount of 14.5%, d.s.b., to the total sugars in the solution. The resulting mixture was mixed to homogeneity, concentrated, dried and pulverized to obtain a pullulan-containing powder with β-cyclodextrin as a non-reducing saccharide. The pullulan-containing powder thus obtained contained 85.1% of pullulan, 12.8% of β-cyclodextrin, 1.1% of glucose, and 1.0% of other oligosaccharides. The percentage of β-cyclodextrin to pullulan was 15.0%, d.s.b.

The product contains pullulan and β-cyclodextrin uniformly with less fear of causing separation of the ingredients, does not lose resistance to humidity, and has a satisfactory rate of water dissolution. Accordingly, the product can be suitably used as a material for food products, cosmetics, and pharmaceuticals, particularly, since the product contains β-cyclodextrin, it can be suitable used in compositions which comprise ingredients susceptible to oxidation, thermal decomposition, light decomposition, etc., or other volatile ingredients.

Example B-1

Pullulan Film

Two hundred and fifty parts by weight of the pullulan-containing powder prepared in Example A-5, 0.5 part by weight of sucrose monolaurate as a surfactant for use as a strippable improver were dissolved in 750 parts by weight of ion-exchange water into a material aqueous solution for preparing pullulan film, followed by deaeration in vacuo. A pullulan film having a thickness of 30 μm was prepared by continuously pouring and extending the material aqueous solution over a synthetic plastic film and drying the applied solution by passing through an atmosphere of 70° hot air.

Since the pullulan film thus obtained has a satisfactory stability against moisture change and an adequate transparency, gloss, and water solubility, it can be advantageously used as an edible, water-soluble material for food products and for fabricating.

Example B-2

Preparation of Sheet

Two hundred and fifty parts by weight of the pullulan-containing powder prepared in Experiment A-3, 25 parts by weight of carboxymethyl cellulose, seven parts by weight of L-ascorbic acid 2-glucoside, 0.1 part by weight of "Kankohso No. 401" i.e, a photosensitizing dye, two parts by weight of ∗-glucosyl rutin, four parts by weight of 1,2-pentandiol, 1.5 parts by weight of N-acylated sodium L-glutamate, acylated by palm oil fatty acid, one part by weight of potassium hydroxide, 0.2 part by weight of sodium ethylenediamine tetraacetate, 0.2 part by weight of sodium citrate, and 0.1 part by weight of citric acid were mixed with and dissolved in 750 parts by weight of deionized water into a material aqueous solution for film, followed by foaming the mixture. A pullulan sheet having a thickness of 100 μm was prepared by continuously pouring and spreading the foamed solution over a synthetic plastic film and drying the applied solution by passing through an atmosphere of 50∗ hot air.

Since the pullulan sheet thus obtained is opaque and has a satisfactory stability against moisture change and an adequate water solubility, it can be used as a material for processing cosmetic face-packs.

Example B-3

Preparation of Capsule

One hundred and fifty parts by weight of the pullulan-containing powder prepared in Example A-1, one part by weight of carrageenan, and three parts by weight of ammonium chloride were dissolved in 850 parts by weight of ion-exchange water into a material aqueous solution, followed by deaerating the solution in vacuo. The obtained solution was heated and kept at 50∗, in which the top of a pinpoint for forming capsules apparatus was dipped, followed taking out the pinpoint from the solution, drying it into a capsule.

Since the capsule contains α,α-trehalose, it has a satisfactory stability against humidity change and an adequate transparency, gloss, and water solubility. Thus, the product can be used as a container for filling food products and pharmaceuticals.

Example B-4

Preparation of Pullulan Fiber

Forty parts by weight of the pullulan-containing powder, prepared in Example A-2, and 0.05 part by weight of locust bean gum were dissolved in 60 parts by weight of ion-exchange water into a material aqueous solution for spinning fibers, which was then extruded in the atmosphere at 30° C. through a nozzle with a diameter of 0.3 mm and a length of 1 mm at a pressing of 2 kg/cm². The moisture in the extruded product was evaporated in the air during it was reeled.

The pullulan fiber thus obtained has a diameter of about 25 μm and can be used as a water-soluble fiber because it has substantially the same time for dissolving in 25° C. hot water as that of a control pullulan fiber prepared with a pullulan product with no non-reducing saccharide, and has a satisfactory stability against drying under a relatively low moisture condition.

Example B-5

Preparation of Shampoo

Twenty parts by weight of the pullulan-containing powder prepared in Example A-3, 15 parts by weight of ethanol, two parts by weight of glycerin, 85 parts by weight of ion-exchange water, 0.3 part by weight of a flavor, 1.5 parts by weight of polyoxyethylene sorbitan monoraulate, and adequate amounts of an antiseptic, antioxidant, and coloring agent were mixed and prepared into a solution.

The solution thus obtained can be advantageously used as a high-quality shampoo because it exerts a satisfactory foam-forming accelerating effect due to pullulan and moisture-retaining effect due to α,α-trehalose after use.

Example B-6

Cosmetic Cream

Fifteen parts by weight of the pullulan-containing powder prepared in Example A4, two parts by weight of polyoxyethylene glycol monostearate, five parts by weight of glyceryl monostearate self-emulsifying, one part by weight of α-glucosyl rutin, one part by weight of liquid paraffin, 10 parts by weight of glyceryl trioctanoate, and five parts by weight of L-ascorbic acid 2-glucoside were dissolved by heating in a conventional manner. To the resulting solution were added two parts by weight of L-lactic acid, five parts by weight of 1,3-butylene glycol, an adequate amount of an antiseptic, and 60 parts by weight of ion-exchange water, followed by emulsifying the mixture by a homogenizer, adding adequate amounts of a flavor and a coloring agent to the homogenate, and stirring and mixing the resultant mixture by mixing to obtain a cream.

Since the cream contains pullulan and α-CD and has a satisfactory smoothness and a relatively highly stabilized ingredients, it can be advantageously used as a high-quality sunscreen or whitening cream.

Example B-7

Preparation of Viscous Soy Sauce

In a commercially available soy sauce was dissolved by heating an adequate amount of the pullulan-containing powder prepared in Example A-1 to obtain a viscous soy sauce with a viscosity of 80 cps, which did not cause separation/precipitation of pullulan and retained its satisfactory viscosity for a relatively long period of time.

When a biscuit-fired rice cake was coated with the soy sauce thus obtained, dried, and observed macroscopically, the pullulan and ∗,∗-trehalose effectively smoothed and glossed the surface of the rice cake. The moisture absorption level of the rice cake after storage was more inhibited compared with a control rice cake, prepared with the above commercialized soy sauce without addition of the pullulan-containing powder.

INDUSTRIAL APPLICABILITY

As evident from the above disclosure, according to the present invention, the pullulan-containing powder with an improved rate of water dissolution is easily prepared in a lesser cost without losing resistance to humidity by preparing a solution which uniformly comprises pullulan and a non-reducing saccharide(s) composed of glucose units, and pulverizing the solution.

Thus, the present invention established a process for producing pullulan-containing powder and provides uses thereof. The pullulan-containing powder is expected to improve the processibility of materials used for preparing shaped products in terms of the fields of applicability of the powder because the powder produced by the process has no fear of casing separation between pullulan and a non-reducing saccharide(s) composed of glucose units, has an improved rate of water dissolution, and does not lose resistance to humidity. Since the shaped products comprising a non-reducing saccharide(s) composed of glucose units, which are produced using the pullulan-containing powder of the present invention, have a satisfactory stability against humidity change, they will be expected for enlarged uses in the fields of food products, cosmetics, pharmaceuticals, etc., in addition to conventional fields of pullulan products with no non-reducing saccharide composed of glucose units, depending on the added values by the non-reducing saccharide(s). Thus, the present invention will greatly contribute to the industrial fields including the above-identified ones.

The invention claimed is:

1. A pullulan-containing powder, which uniformly comprises
   pullulan as a main ingredient and amorphous α-cyclodextrin,
   which powder contains at least 85 w/w % of said pullulan with respect to the weight of said powder and at least 10 w/w % but not more than 15 w/w % of α-cyclodextrin with respect to the weight of said pullulan in the powder, and
   which powder is produced by pulverizing a homogeneous solution containing pullulan and said amorphous α-cyclodextrin.

2. A composition comprising the pullulan containing powder of claim 1, wherein said composition also contains food products, cosmetics, or pharmaceuticals.

3. The composition according to claim 2, which is in the form of a solid product.

\* \* \* \* \*